(12) United States Patent
Floratos et al.

(10) Patent No.: US 6,205,444 B1
(45) Date of Patent: Mar. 20, 2001

(54) MULTIPLE SEQUENCE ALIGNMENT SYSTEM AND METHOD

(75) Inventors: Aris Floratos, Long Island City; Laxmi P. Parida, New York; Isidore Rigoutsos, Astoria, all of NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 09/174,036

(22) Filed: Oct. 16, 1998

Related U.S. Application Data

(60) Provisional application No. 60/062,306, filed on Oct. 17, 1997.

(51) Int. Cl.[7] ................................................. G06F 17/30
(52) U.S. Cl. ................................. 707/6; 707/101; 341/55
(58) Field of Search ............................. 707/6, 101, 100, 707/104; 341/55; 706/47

(56) References Cited

U.S. PATENT DOCUMENTS

| | | | |
|---|---|---|---|
| 5,897,637 | * 4/1999 | Guha | 707/101 |
| 5,930,789 | * 7/1999 | Agrawal et al. | 707/6 |
| 5,977,890 | * 11/1999 | Rigoutsos et al. | 341/55 |
| 5,983,224 | * 11/1999 | Singh et al. | 707/6 |
| 6,061,682 | * 5/2000 | Agrawall et al. | 707/6 |
| 6,092,065 | * 7/2000 | Floratos et al. | 707/6 |
| 6,094,645 | * 7/2000 | Agrawal et al. | 706/47 |

OTHER PUBLICATIONS

Agrawal et al., "Mining Sequential Patterns", IEEE Computer Society Press, 1063–6382, pp. 25–33, Mar. 1995.*

* cited by examiner

Primary Examiner—Paul R. Lintz
(74) Attorney, Agent, or Firm—F. Chau & Associates, LLP

(57) ABSTRACT

The method of the present invention aligns a set of N sequences, where N is large. The alignment brings out the best commonality of the N sequences. The method is performed in two stages. A first stage involving discovering motifs, and a second stage involve motif pruning and sequence alignment. The present invention also provides an additional constraint, K, as a user defined control parameter. The additional parameter constrains the alignment of the N sequences to have at least K of the N sequences agree on a character, whenever possible, in the alignment. The alignment number, K, provides a natural constraint for dealing with a large number of sequences in that a commonality across most, if not all sequences is required to be detected.

39 Claims, 12 Drawing Sheets

FIG. IA

Sequence 1 = A G H D X Y L M B T S
Sequence 2 = A I C D J F T S L M B
Sequence 3 = X Y C D K F Motif 1 = "A . . D"  10,
Motif 2 = "C D . F"  12,
Motif 3 = "X Y"       14,
Motif 4 = "L M B"    16,
Motif 5 = "T S"       18.

FIG. IB

SEQUENCE 1

```
( 1)  ARTKQTARKSTGGKAPRKQL.TKAA.K.AP..GGVKKPH..RPGTVAL
( 2)  ARTKQTA.KSTGGKAPRKQL..KAA.K.AP..GGVKKPH...PGTVAL
( 3)  ARTKQTARKSTGGKAPRKQL.TKAA.K.AP..GGVKKPH..RPGTVAL
( 4)  ARTKQTARKSTGGKAPRKQL.TKAA.K.AP..GGVKKPH..RPGTVAL
( 5)  ARTKQTARKSTGGKAPRKQL.TKAA.K.AP..GGVKKPH..RPGTVAL
( 6)  ARTKQTA.KSTG.KAPRKQL.TKAA.K.AP..GGVKKPH..RPGTVAL
( 7)  ══R.S..G.A.R.Q..TK.A......GGVK........V—
( 8)  ARTKQTARKSTGGKAPRKQL.TKAA.K.AP..GGVKKPH..RPGTVAL
( 9)  ARTKQTARKSTGGKAPRKQL.TKAA.K.AP..GGVKKPH..RPGTVAL
(10)  ARTKQTARKSTGGKAPRKQL.TKAA.K.AP..GGVKKPH..RPGTVAL
(11)  ARTKQTARKSTGGKAPRKQL.TKAA.K.AP..GGVKKPH..RPGTVAL
(12)  ARTKQTARKSTGGKAPRKQL.TKAA.K.AP..GGVKKPH..RPGTVAL
(13)  ARTKQTA.KSTGGKAPRKQL..KAA.K.AP..GGVKKPH...PGTVAL
(14)  ══R.S...........TK.A......GGVK—————
(15)  ══R.S...........TK.A......GGVK—————
(16)  sg–R.K......GG.A.Rhrkvlrdni......GGVK—————
(17)  sg–R.K......GG.A.Rhrkvlrdni......GGVK—————
(18)  sg–R.K......GG.A.Rhrkvlrdni......GGVK—————
(19)  sg–R.K......GG.A.Rhrkvlrdni......GGVK—————
(20)  sg–R.K......GG.A.Rhrkvlrdni......GGVK........V—
```

SEQUENCE 1 (CNT'D)

```
( 1)  REIRRYQKSTELLIR..PFQRLVREIAQDFKT.LRFQ.SAV.ALQEA.EAYL
( 2)  REIRR.QKSTELLIR..PFQRLVREIAQDFKT.LRFQ.SA..ALQE..EAYL
( 3)  REIRRYQKSTELLIR..PFQRLVREIAQDFKT.LRFQ.SAV.ALQEA.EAYL
( 4)  REIRRYQKSTELLIR..PFQRLVREIAQDFKT.LRFQ.SAV.ALQEA.EAYL
( 5)  REIRRYQKSTELLIR..PFQRLVREIAQDFKT.LRFQ..A..ALQEA.EAYL
( 6)  .EI.RYQKSTELLI...PFQRLVREIAQDFKT.LRFQ.SAV.ALQEA.EAYL
( 7)  ———R...STELLI...PFQRLV.EIAQDFKT.LRFQ..A..ALQEA.EA..
( 8)  REIRRYQKSTELLIR..PFQRLVREIAQDFKT.LRFQ.SAV.ALQEA.EAYL
( 9)  REIRRYQKSTELLIR..PFQRLVREIAQDFKT.LRFQ.SAV.ALQEA.EAYL
(10)  .EI..YQKSTELLIR..PFQRLVREIAQDFKT.LRFQ.SAV.ALQEA.EAYL
(11)  REIRRYQKSTELLIR..PFQRLVREIAQDFKT.LRFQ.SAV.ALQEA.EAYL
(12)  REIRRYQKSTELLIR..PFQRLVREIAQDFKT.LRFQ.SAV.ALQEA.EAYL
```

| FIG. 5 |
|---|
| FIG. 5A |
| FIG. 5B |
| FIG. 5C |
| FIG. 5D |
| FIG. 5E |
| FIG. 5F |
| FIG. 5G |
| FIG. 5H |

FIG. 5A

(13) REI RR. QKSTELLI R. . PFQRLVREI AQDFKT. LRFQ. SA. . ALQE. . EAYL
(14) R. . RR————L. R. . . . . R. . . . I . . D . . . . L . . . . . . V————
(15) R. . RR————L. R. . . . . R. . . . I . . D . . . . L . . . . . . V————
(16) R. . RR————L. R. . . . . R. . . . I . . . . . . . Lkvflen————
(17) R. . RR————L. R. . . . . R. . . . I . . . . . . . Lkvflen————
(18) R. . RRggvkrisa————LV. Eetravlklflen————
(19) R. . RR————L. R. . . . . R. . . . I . . . . . . . Lkiflen————
(20) R. . RR————L. R. . . . . R. . . . I . . . . . . . Lks. . .S . . . . . . . . . E——

SEQUENCE 1 (CNT'D)

( 1) V. LFEDTNLCAI HAKRVTI MPKDI QL. RRI RGERA
( 2) V. LFEDTNL. AI H. KRVTI . . KD. . L. RR. RGER
( 3) V. LFEDTNLCAI HAKRVTI MPKDI QL. RRI RGERA
( 4) V. LFEDTNLCAI HAKRVTI MPKDI QL. RRI RGERA
( 5) V. LFEDTNLCAI HAKRVTI MPKDI QL. RRI RGERA
( 6) V. LFEDTNLCAI HAKRV. I MPKDI QL. RRI RGERA
( 7) V. LFEDTNLCAI HAK. VT. . PKDI QL. . . I . GERA
( 8) V. LFEDTNLCAI HAKRVTI MPKDI QL. RRI RGERA
( 9) V. LFEDTNLCAI HAKRVTI MPKDI QL. RRI RGERA
(10) V. LFEDTNLCAI HAKRVTI MPKDI QL. RRI RGERA
(11) V. LFEDTNLCAI HAKRVTI MPKDI QL. RRI RGERA
(12) V. LFEDTNLCAI HAKRVTI MPKDI QL. RRI RGERA
(13) V. LFEDTNL. AI H. KRVTI . . KD. . L. RR. RGER
(14) V. . . . .T. . . . . . . .K. VT. . . . . . . .L. R. . Rtlygfgg
(15) V. . . . .T. . . . . . . .K. VT. . . . . . . .L. R. . Rtlygfgg
(16) V. . . . .T. . . . . . . .K. VT. . . . . . . .L. R. . Rtlygfgg
(17) V. . . . .T. . . . . . . .K. VT. . . . . . . .L. R. . Rtlygfgg
(18) V. . . . .T. . . . . . . .K. VT. . . . . . . .L. R. . Rtlygfgg
(19) V. . . . .T. . . . . . . .K. VT. . . . . . . .L. R. . Rtlygfgg
(20) V. . . . .T. . . . . . . .K. VT. . . . . . . .L. R. . Rtlygfgg

SEQUENCE 2

( 1) IIpkppahhphyafrfl DLFAGI GG. . . GFE. . G = E. . . . A. . . Y. . N ==
( 2)     mskanakysfv-DLFAGI GG. . . . L. . . G = E. D. . A. . . Y. . N ==
( 3)       mekkl I . LF. G. GG. . . GF. . AG = ———————— ==
( 4)       mkfrkge—LF. G. GG. . LG. . . Ak = ekfgei———— ==

FIG. 5B

```
(  5) sndeiqyksdkfnvls—LF.G.GG..LGFE.AG  ==  ———A...Y..N  ==
(  6)             mkvls—LF.G.GG..LGLE——   ==  ——————————  ==
(  7)       mqqfrfl DLFAGI GG..LGLE..G    ==  E.D..A...Y..N  ==
(  8)          mlqias—LFAG.GG..LGFE..G    ==  E.D..A...Y..N  ==
(  9)         mkikfv–DLFAGI GG...GFE.A    ==  E.D..A...Y..N  ==
( 10)         msklrvms—LF.GlG.....L...G   ==  E.D..A...Ycai  ==
( 11) tnnnfekqnrgikltfl DLFAGI GG..LGFE—— ==  E.D..A...Y..N  ==
( 12)         msklrvms—LF.GlG.....L...G   ==  E.D..A...Ycai  ==
( 13) iiekvdfrtdkinvts—LF.G.GG..LGFE.AG   ==  ———A...Y..N    ==
( 14)         msklrvms—LF.GlG.....L...G   ==  E.D..A...Ycai  ==
( 15)         mgklrvms—LF.GlG.....L...G   ==  ——————————     ==
( 16)         msfrtle—LF.Gl......Lrgis    ==  ——————————     ==
( 17)           mlkfl DLFAGI GG..LGFE.A-  ==  E.D..A...Y..N  ==
( 18)          mkqfrfl DLFAGI GG..LGLE..G ==  E.D..A...Y..N  ==
( 19)            mnil DLFAG.GG...GF..AG   ==  E.D..A...Y..N  ==
( 20)             mktl DLFAG.GG..LGF..AG  ==  ———A...Y..N    ==
( 21)         mvgavl DLF.G.GG...GL...G    ==  ——————————     ==
( 22) ivkpveppkeirlatl –D.FAG.GG...GL..AG ==  anelaaklteeqk  ==
( 23) psepeieiklpklrtl –D.F.G.GG...GF..AG ==  kgdvem———      ==
( 24) pkepeaaiklpklrtl –D.F.G.GG...GF..AG ==  kgdvem———      ==
( 25)            mkcv–DLF.G.GG..LGFE.AG   ==  E....A...Y..N  ==
( 26)       mqqfrfl DLFAGI GG..LGLE..G    ==  E.D..A...Y..N  ==
( 27) mlpeapahhpdyafrfl DLFAGI GG...GFE..G ==  E....A...Y..N ==
( 28)           mklls—LF.G.GG..LGFE.AG    ==  ——————————     ==
( 29)     mkknimglslfssa————Gl Geyflsrvgid ==  ——————————    ==
( 30)            mktl DLFAG.GG..LGF..AG   ==  ———A...Y..N    ==
( 31)     mkinamslfssa————Gl Geldlhkgnln  ==  ——————————     ==
( 32) mieikdkqltglrfl DLFAG.GG..L.LE..G   ==  E.D..A...Y..N  ==
( 33) lfepesnpnlrekftfl DLFAGI GG........G ==  E.D..A...Y..N ==
( 34)             mnll.LF.G.GG..LGF..AG   ==  ——————————     ==
( 35)          mnmdiasf——F.G.GG..LGF..AG  ==  ——————————     ==
( 36) thieerkdayssdfkfl DLF.GlGG.....E..G ==  E.D..A...Y..N  ==
( 37)             mkil.LF.G.GG..LGFE.AG   ==  ——————————     ==
( 38) lrlnrpdwnviegdvr—LF.G.G.....L...G   ==  ——————————     ==
( 39)          mfkil DLFAGI GG..LGFE.A-   ==  E.D..A...Y..N  ==
( 40) pdtppypnnengryrml DLFAGI GG..LGF—— ==  E.D..A...Y..N   ==
( 41)        mnkikvve—LFAG.GG..LGLE———    ==  ——————————     ==
( 42) dvsnvrknkdynvfet——FAG.GG..LGLE.AG   ==  ——————————     ==
```

FIG. 5C

(43) pei apfenrkt akykml DLFAGI GG..LGF———   = E.D..A...Y..N =
(44)              ml rvfea——FAG.G.....Li kan  = ktfenradkl ggq =
(45) tedi l kl agvssgnei ——————————————  = ——————————— =
(46) mskvenkt kkl rvfea——FAGI G.....L——  = ——————————— =

SEQUENCE 2 (CNT'D)

( 1) P..D.L..GFPCQ.FS.AG......D.RG.LF....RI.....
( 2) ——D.L.GGFPCQ.FS..G...G....RG.LF....RI.....
( 3) ——D...GG.PCQ.FS.AGKR.G..D.RG.L......R.....
( 4) ——D....GFPC...S..G...G.....G.L———┤
( 5) P......GGFPC..FS.AG.R———D....L......R.....
( 6) ——D...GGFPCQ.FS.AGKR.GF————————————
( 7) P..D...GG.PCQ..S.AGK...F.D.RG.L......R.....
( 8) P..D.L..GFPC..FS.AG.R.GF.D——G.LF....R.....
( 9) P..D.L..GFPCQ.FS.AGK..GF.D.RG.LF....R.....
(10) P..D.L..GFPC..FS.AG.R.G——D.RG.LF...........
(11) P..D.L..GFPCQ.FS..GKR.GF...————————RI.....
(12) P..D.L..GFPC..FS.AG.R.G——D.RG.LF...........
(13) P......GGFPC..FS.AG.R....D....L......R.....
(14) P..D.L.GG.PCQ.FS.AG.R.GF.D.RG.LF...........
(15) P..D.L.GG.PCQ.FS.AG.R.GF.D.RG.LF...........
(16) ——D....GFPC..FS.AG.R.GF————L......R.....
(17) P..D.L..GFPCQ.FS.AGK..GF.D.RG.LF....RI.....
(18) P..D...GG.PCQ..S.AGK...F.D.RG.L......R.....
(19) ——D...GG.PCQ.FS..G.R———D....LF....R.....
(20) ————GG.PCQ.FS.AGKR————————————┤.....
(21) ————————PCQ..Sqytkksrtgtkwq–L......R.....
(22) ——D...GG.PCQ..S——————————————————
(23) ————L.GG.PCQ.FS——————————————————
(24) ————L.GG.PCQ.FS——————————————————
(25) ——D...GG.PCQ.FS.AGKR————————————┤.....
(26) P..D...GG.PCQ..S.AGK...F.D.RG.L......R.....
(27) P..D.L..GFPCQ.FS.AG........RG.LF....RI.....
(28) P..D...GG.PCQ..S.AG...G..D.RG.LF....RI.....
(29) ————————PCQ..S.AGKnrdvsnmandnrnyl i myvi ami
(30) ————GG.PCQ.FS.AGKR————————————┤.....
(31) ————————PCQ..S..GKnkhqdh——————————
(32) P..D.L..GFPCQ.FS..GK..GF.D.RG.LF....RI.....

FIG. 5D

(33)  —D. L. . GFPCQ. FS. AGKR. GF. D. RG. LF. . . . RI . . . . .
(34)  P. . D. . . GG. PCQ. . S. . G. . . G. . D. RG. LF. . . . RI . . . . .
(35)  P. . . . . . GG. PCQ. . S. AG. . . G. . D. RG. . F————
(36)  P. . D. L. . GFPCQ. FS. . GKR. GF——————————
(37)  —D. . . GG. PCQ. . S. AG. . . G. . D. RG. LF. . . . RI . . . . .
(38)  —D. L. GG. PC. . FS. AGK. . G. . D. . . . LF. . . . R. . . . . .
(39)  P. . D. L. . GFPCQ. FS. AG. . . GF. D. RG. LF. . . . RI . . . . .
(40)  P. . . . L. GGFPC. . FS. AG. . . GF. D. RG. LF. . . . RI . . . . .
(41)  —D. . . GGFPCQ. . S. A————————G. LF. . . . R. . . . . .
(42)  —D. L. GG. PCQ. FS. AGKR. GF. D. RG. LF. . . . . I . . . . .
(43)  P. . D. L. GGFPCQ. FS. AGK. . GF. D. RG. LF. . . . RI . . . . .
(44)  dfftys——FPCQ. . S. AG. . . G. . . . . Gfrssllwecck. . .
(45)  —D. . . GG. PCQ. FS. AGKR. G. . D. RG. . F————
(46)  ———L. . . FPCQ. . S. . G. . . G. . . . . Gfrsgllweierald

SEQUENCE 2 (CNT'D)

( 1)  P. . F. LENVK. L. . . . . G = GY. . . . . . . Ngpddpkiidgkhfl. VG
( 2)  P. . . . LENV. . L———— = ————L. A. . . G. PQ. RERV. I
( 3)  P. . F. . ENVKG. . . . . . G = -Y. . . . . . LNA. D. GVPQ. RERV. IVG
( 4)  P. . F. . ENV. GL. . . . . G = ——————YGVPQ. R. R. . IVG
( 5)  P. . F. . ENVKG. . . . . . G = GY. . . . . . LNA. DYGVPQ. RERV. IVG
( 6)  P. . F. . ENVKG———— = ————LNA. . YGV. Q. RERV. . . G
( 7)  P. . F. . ENVKG———— = GY. . . . . . LN. . . . GV. Q. R. RV. IVG
( 8)  P. . . . LENVK. L. . . . . G = GY. . . . . . LNA. D. G-PQ. RER. . IVG
( 9)  P. . F. LENV. GL. . . . . G = GY. . . . . . LN. . . . GVPQ. R. R. . I. G
(10)  P =
(11)  P. . F. LENVKGL. . . . . G = -Y. . . . . . . . A. . . G. PQ. RER. . IVG
(12)  P. . . . LENVKGL. . . . . G = GY. . . . . . LN. . . . . VPQ. RERV. I. G
(13)  P. . F. . ENVKG. . . . . . G = GY. . . . . . LNA. DYGVPQ. RERV. IVG
(14)  P. . F. . ENVKGL. . . . . G = GY. . . . . . LN. . . . . VPQ. RER. . I. G
(15)  P. . F. . ENVKGL. . . . . G = GY. . . . . . LN. . . . . VPQ. RER. . I. G
(16)  P. . . . LEN =
(17)  P. . F. LENV. GL. . . . . G = ————LN. . . . . VPQ. R. RV. IVG
(18)  P. . F. . ENVKGL———— = GY. . . . . . LN. . . YGV. Q. R. RV. I. G
(19)  P. . F. . ENV. G———— = GY. . . . . . LNA. DYGVPQ. RV. . . G
(20)  P. . . . . ENV———— = GY. . . . . . L. A. . . GVPQ. R. R. . . . G
(21)  P. . . . . ENV. . . . . . . . G = ——————————YG. PQ. R. R
(22)  P. . . . LENV. . . . . . . . G = GY. . . . . . L. A. . YGV. Q. R. R. . I

FIG. 5E

```
(23)  P....LENV————     == GY......L.A..YGV.Q.R.R..I
(24)  P....LENV————     == GY......L.A..YGV.Q.R.R..I
(25)  P.....ENV————     == GY......L.A...GVPQ.R.R....G
(26)  P..F..ENVKGL———   == GY......LN....GV.Q.R.RV.IVG
(27)  P..F.LENVK.L.....G == ————————PQ.RER...VG
(28)  P..F..ENVKG————   == GY......LNA.DYGV.Q.RERV..VG
(29)  kklk..ENV..L————  == -Y......L.A.DYG.PQ.R.R..I
(30)  P.....ENV-Y......LNA.DYG.PQ.RER
(31)  ——F...N...Lifevfe == nvprfiemyfpyngqlllleeilkikyask
(32)  P.....ENVK.......G ==
(33)  P..F.LENVKGL.....G == ————————NA...GVPQ.RER..IVG
(34)  P..F..ENVKG————   == GY......LNA.DYGV.Q.R.RV...G
(35)  P..F..ENV.G————   == GY......LNA.DYGVPQ.R.RV.IVG
(36)  ————LENV.GL.....G == GY......L.A...G.PQ.R.R...Vaflnqnihfe
(37)  P..F..ENV.G————   == GY......NA.DYGV.Q.R.RV...G
(38)  P....LENV.GL————  == GY......L.A.DYG..Q.R.RV..Valkneytnff
(39)  P..F.LENVK.L.....G == GY......L.A.D.G.PQ.RER...VG
(40)  P..F.LENVK.L.....G == -Y.......A.D.GVPQ.RER..IVG
(41)  P....LENV..L————  == GY......NA.DYG..Q.R.RV.I.G
(42)  P..F..ENV.GL.....G == GY......LN.....V.Q.RER..I.G
(43)  P..F.LENVK.L.....G == -Y.......A.D.G.PQ.RER..IVG
(44)  P.....ENVK.L————  == GY......LNA.D.G.PQ.RERV
(45)  P.....ENV.GL————  == GY......N....GVPQ.RERV.I
(46)  stekndlNV..L————  == GY......LNA.D.G..Q.R.RV
```

SEQUENCE 3

```
( 1)       altekqeal...s.e..k.n.p..s.......i.e.ap..k..fsflkdsn
( 2)       mstlegrgFTe.QEALV..S....K.N.......F...I.E.AP.A..IFsfLkdsn
( 3)       sssevnkvFTe.QEALV.......K.N.......F...I.E.AP.Ak.IFs.Lkdsp
( 4)       msssevdkvFTe.QEALV..S....K.N.......F...I.E.AP.Ak.IFs.Lkdsp
( 5)       gvlt..q.alv.ss.e.f..n.p.....f....le.ap.ak.Ifsflkgsse
( 6)       msFT.KQEALV.sS.E.FK.N.p..s..Fy...IEkAPaAk.IFsfLknsa
( 7)       msFT.KQEALV.sS.E.FK.N....s..Fy..IIEkAPaAk.IFsfLkdsa
( 8)       gFT.KQEALV.sS.Ef————k.n.p..s..fy...Iekapaak.Ifsflk
( 9)       gaFTeKQEALV.sS.E.FK.N.p..s..Fy..IIEkAPaAk.IFsfLangv
```

FIG. 5F

(10)  gFTeKQEALV.sS...FK.N....s..Fy..II.kAP.Ak..FsfLkdsa
(11)  galte.q.alv.ss.e.f...n.p.....f....le.apaak.lfsflkgtse
(12)  mgFTeKQEALV.sS.E.FK.N.p..s..fy..ilekapaak..fsflkdta
(13)  gFTeKQEALV..S.E.FK.N.p..s..Fy..IIEkaPaAk..FsfLkdsd
(14)  gaFTeKQEALV.sS.E.FK.N.p..s..Fy..IIEkaPaAk.IFsfLsngv
(15)  mgFT.KQEALV.sS.E.FK.N.p..s..fy..ilekapaak..fsflkdsa
(16)  gFTeKQEALV..S.E.FK.N.p..s..Fy..IIEkaPaAk..FsfLkdfd
(17)  gaFT.KQEALV.sS.E.FK.N.p..s..Fy..IIEkaP.Ak.IFsfLangv
(18)  mgFT..QEALV.sS.E.FK.N.p..s..Fy..IIEkaPaAk..FsfLkdsa
(19)  gaFTeKQEALV.sS.E.FK.N.p..s..Fy..IIEkaPaAk.IFsfLangv
(20)  vaFTeKQ.ALV.sS.E.FK.N.p..s..Fy..IIEkaPaAk.IFsfLangv
(21)  mggFTeKQ.ALV.sS.E.FK.N.p..s..Fy..IIEkaPaAk.IF.fLangv

SEQUENCE 3 (CNT'D)

( 1)  ei pen——NPkL..HA...F.....sA..Lr..G..vwdn=LG.iH......DP
( 2)  vpl er——NPkL..HA..vF.....sA.qLr..G.vtvr=kLG..H...GV.D-
( 3)  vpl eq——NPkL..HA..vF.....sA.qLr..Gkatv=sdlg.ih...gv...
( 4)  ipl eq——NPkL..HA..vF.....sA.qLr..G=.snlkrLG.ih...gv——
( 5)  vpqn——NP.L..HA.kvF......A.qL...G.vasda=LG..H..KGV.D.
( 6)  evqds——p.L..haekvf..vrdsa.qlr...g.vv...atLG.iH.KGV.DP
( 7)  gvqds——p.L..haekvf..vrdsa.qlr...g.vv...aaLG.iH.KGV.DP
( 8)  dtagveds—pkl..hae.vf..vrdsa.qlr...g.vv...atLG.iH.KGV..P
( 9)  dpt———NPkL..HAeK.F..vrdsA.ql...G.vv...a-L..iH..K.V.DP
(10)  gvvds——pkl..haekvf..vrdsa.qlr...g.vvldgkd+g.ih..kgv.dp
(11)  vpqn——NP.L..HA.kvf..v...A.qL...G.vvtda=LG..H..KGV.D.
(12)  gvqd——s-pkl..haekvf..vrdsa.qLr...g.vv...atLG.iH..KGV.DP
(13)  gvpqn——NP.L..HAekvF..vrdsA.qLr...G.vv...asLG..H..KGV.DP
(14)  dps———NPkL..HAek.F..vrdsA.qL...G.vv...a-LG.iH..K...DP
(15)  gvqd——s-pkl..haekvf..vrdsa.qLr...g.vv...atLG.iH..KGV.DP
(16)  evpqn——NP.L..HAekvF..vrdsA.qLr...G.vv...asLG..H..KGV.DP
(17)  dpt ———NPkL..HAek.F..vrdsA.qL...G.vv...a-LG.iH..K...DP
(18)  gvqds———p.l..haekvf..vrdsa.qlr...g.vv...atLG.iH..KGV.DP
(19)  dpt ———NPkL..HAe..F..vrdsA.qLr...G.vv...a-LG.iH..KGV...
(20)  dpt ———NPkL..HAek.F..vrdsA.qL...G.vv...a-LG..H..K.V.DP
(21)  dpt ———NPkL..HAek.F..v.dsA.qLr...G.vv...a-LG..H..KGV.DP

SEQUENCE 3 (CNT'D)

( 1)  hF.V.K.ALL.TIKEA....WS.E...AW..AY..L...IK..mke

FIG. 5G

```
( 2) hF. V. K. ALL. TI KEA. . . . WS. E. . . AW. . AYD. L. . al K. . mkpss
( 3) hf. v. . . al l . ti kea. . . . ws. e. . . aw. vayd. l . . ai k. . mkpsst
( 4) hFetrf-al l . ti kea. . . . ws. e. . . aw. . ayd. l . . ai k. . mkpsst
( 5) hF. VVKEA. LKTI KE. . G. . WS. EL. . AW. . AYD. LA. . I KK. mkdaa
( 6) hF. VVKEALLKTI KEA. G. . WS. EL. . AW. vAYD. LA. al KK. ms
( 7) hF. VVKEALLKTI KEA. G. . WS. EL. . AW. vAYD. LA. . I KK. ms
( 8) hF. VVKEALL. TI K. A. G. . WS. EL. . AW. vAYD. LA. al KK. mkt a
( 9) . F. VVKEALLKTI KEA. G. . WS. EL. . AW. vAYD. LA. al KKa
(10) hf. vvkeal l kti kea. g. . ws. el . . aw. vayd. l a. ai kaa
(11) hF. VVKEA. LKTI KE. . G. . WS. EL. . AW. . AYD. LA. . I KK. mndaa
(12) hF. VVKEALLKTI KE. . G. . WS. EL. . AW. vAYD. LA. al KK. mg
(13) hF. VVKEALLKT. KEA. G. . WS. E. . . AW. vAYD. L. . al KK. ms
(14) . F. VVKEALLKTI KEA. G. . WS. EL. . AW. vAYD. LA. al KKaf
(15) hF. VVKEALLKTI KE. . G. . WS. EL. . AW. vAYD. LA. al KK. mv
(16) hF. VVKEALLKT. KEA. G. . WS. E. . . AW. vAYD. L. . al KK. ms
(17) . F. VVKEALLKTI KEA. G. . WS. EL. . AW. vAYD. LA. al KKaf
(18) hF. VVKEALLKTI KEA. G. . WS. E. . . . W. vAYD. LA. al KK. ms
(19) . F. VVKEALLKT. K. A. G. . W. . . L. . A. . . AYD. LA. al KKaya
(20) . F. VVKEALLKTI K. A. G. . WS. EL. . AW. vAYD. LA. al KKa
(21) . F. VVKEALLKT. KEA. G. . WS. EL. . AW. vAY. . LA. a. KKaf
```

FIG. 5H

MULTIPLE SEQUENCE ALIGNMENT SYSTEM AND METHOD

CROSS-REFERENCE TO RELATED APPLICATIONS

The present application claims priority to Provisional U.S. Patent Application No. 60/062,306, filed Oct. 17, 1997 by A. Floratos and I. Rigoutsos, herein incorporated by reference in its entirety.

BACKGROUND OF THE INVENTION

1. Field of the Invention

The present invention relates to the field of aligning data sequences, and, more specifically, to a method and system for aligning multiple data sequences to achieve the best commonality of the sequences.

2. Discussion of the Prior Art

The problem of aligning a large number of sequences appears very often and in many different application areas (e.g. biology, data mining in databases, computer security etc.). It has been observed that most traditional methods of aligning multiple sequences do not work well on large number of sequences on the order of N>10.

The multiple sequence alignment problem has been studied for at least the last fifteen years, in the context of Computational Biology, it is well known that this is a rather difficult problem. Contributing to the difficulty in solving the problem is that in its most general form, it is difficult to model to the satisfaction of Evolutionary Biologists, Geneticists and other users. The most popular and successful approach to date has been a dynamic programming technique using different mechanisms of scores that is a function of the edit distance along with gap penalties to evaluate the similarity of the different sequences. Dynamic programming relies on identifying good penalty scores for matches and mis-matches. This is difficult to realize in real-world applications. The method is best suited to small sequence numbers on the order of N<6.

For the situation where there are more than two sequences to be aligned, one of the prior art approaches has been to perform a pairwise alignment where two of the N sequences are analyzed at a time and an N-wise alignment is built from the pairwise alignments. This approach works well for small values of N on the order of N<6, however, for large values of N additional constraints are required to give meaningful alignments.

It is apparent that the problem of aligning multiple sequences where the number of sequences is large is computationally a very demanding one.

SUMMARY OF THE INVENTION

The problems stated above and the related problems of the prior art are solved with the method and system according to the present invention. A method is provided that is specifically suited to aligning a large number of sequences, on the order of N>10, simultaneously, that brings out the best commonality of the N-sequences. The method is built on top of an existing method for identifying or discovering motifs in sequences. A motif can be informally defined as a repeated pattern that appears in two or more input sequences. The method uses some, if not all, of these identified motifs to give a good alignment. The present invention also provides an additional constraint, K, as a user defined control parameter. The additional parameter constrains the alignment of the N sequences to have at least K of the N sequences agree on a character, whenever possible, in the alignment. The alignment number, K, provides a natural constraint for dealing with a large number of sequences in that a commonality across most, if not all sequences is required to be detected.

Given a set of N input character sequences, the present invention aligns the N sequences in a way that brings out the best commonality of the N character sequences. At a motif discovery stage, the method of the present invention first identifies any motifs which may exist in the input sequences. At a pruning and alignment stage, the method detects one or more infeasible sets from the motifs identified at the motif discovery stage. Each infeasible set is comprised of a subset of those identified motifs which preclude an alignment which brings out the best commonality. Once identified, one or more motifs from the infeasible sets are removed ("pruned"), from consideration when aligning the sequences at an alignment stage. The remaining motifs comprise a feasible set which is then used to align or render the sequences to maximize a pre-specified cost function.

The sequence alignment method of the present invention is advantageous for the following reasons; 1) The approach is efficient, particularly on large numbers of long sequences, 2) a direct N-wise alignment is achieved by not composing the alignments from lower order (pairwise) alignments as practiced in the prior art, 3) the approach is adaptable to underlying biological or other models, using the idea of in-exact motif, 4) it allows for easy user intervention and specification in terms of which motif the user must have in the alignments, 5) it gives various alternate solutions, if required, to the user based on different configurations that the user wants to see rather than give a cost value which the user may or may not be able to relate to, 6) the resulting alignment is independent of the order of the input sequences.

The invention and its operation will become more apparent from the following description of an exemplary embodiment and from the accompanying drawings.

BRIEF DESCRIPTION OF THE DRAWINGS

FIG. 5 Experimental results that illustrate the method of the present invention as applied to biological data.

DETAILED DESCRIPTION OF PREFERRED EMBODIMENTS

Figure 1:
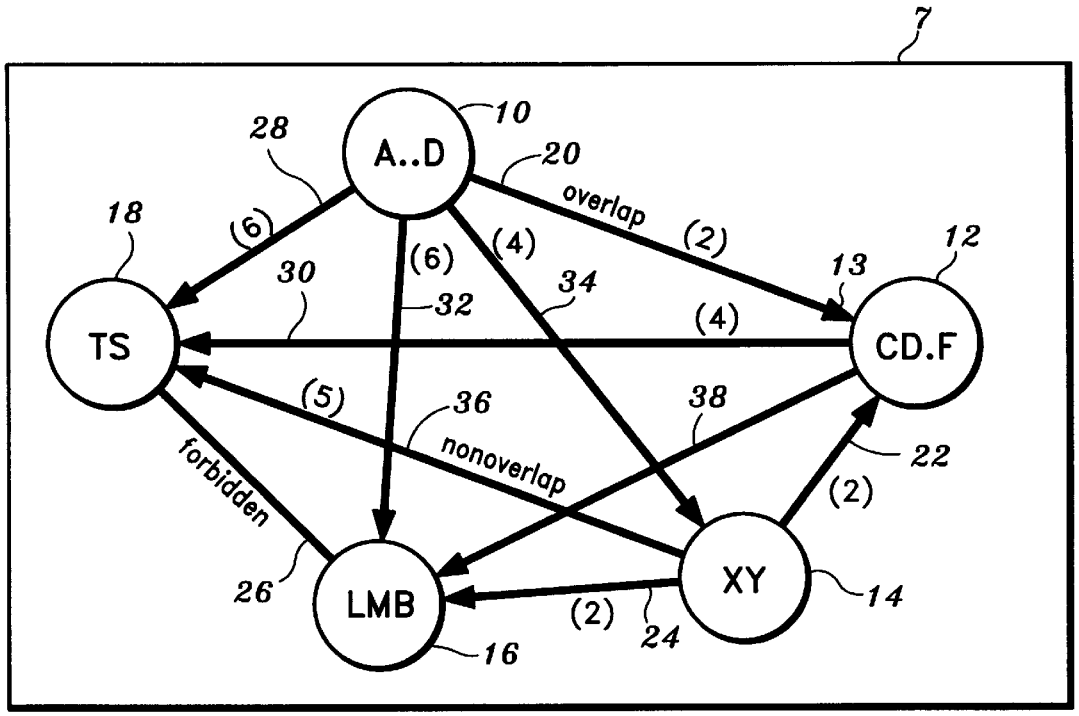
FIGS. 1$a$&$b$ show a directed graph and associated input sequence and corresponding identified motifs from which the graph is derived.

The subject invention will be described with reference to numerous details set forth below and the accompanying drawings which illustrate the invention. The following description is illustrative of the invention and is not to be construed as limiting the invention. Numerous specific details are described to provide a thorough understanding of the present invention. It will be apparent, however, to one of ordinary skill in the art that the present invention may be practiced without these specific details. In other instances, certain well known or conventional details are not described to preclude obscuring the present invention in detail.

The method of the present invention may be implemented as a computer program readable by a general purpose computer for executing computer instructions directed to aligning multiple sequences to bring out the best commonality of the sequences.

Overview

To better appreciate the sequence alignment method of the present invention, an illustrative example is provided:

Generally, a sequence is a string of characters taken from a finite character set or alphabet. As an arbitrary example, the following sequences could have arose from the English alphabet.

sequence 1: W <u>A B C</u> G Z T V <u>A Q C</u> B H N G Z T sequence 2: <u>A P C</u> G Z E <u>A T C</u> T V B H N W <u>A B C</u> A Y sequence 3: U I W D V P L H R Q Z S D A pattern is a specific set of characters of any length from an alphabet where the pattern has a particular spatial arrangement. An example of such a pattern from sequence 1 above would be "G Z T", or from sequence 2, "V B H". Any combination of consecutive letters from any of the sequences would constitute a valid pattern. Patterns may also contain "don't care" characters such as "A . C", where the dots are used to indicate that the respective position could be occupied by "any" character (don't care character). Any character which is not a don't care character, such as "A" and "C" in the pattern, is referred to as a solid character.

As previously stated, the present invention is partially directed to the process of motif discovery or identification. As defined in the prior art, a motif is a repeated pattern that appears more than once in a sequence. For the example provided, the pattern "G Z T" qualifies as a motif in sequence 1 above under the prior art definition. In the context of the present application, however, a motif is defined as a pattern that appears in two or more sequences. Under the present definition the pattern "A . C" qualifies as a motif in the example above because it appears in at least two sequences, the first and the second.

The sequence alignment method of the present invention solves the following problem.

Problem:

Given a set N of sequences each of length $n_1, n_2, \ldots, n_N$ on any alphabet set, and an alignment number K, where $((2<=K<=N))$, as input, align the N sequences in such a way that brings out the best commonality of the N sequences, with the possible introduction of gaps.

The problem formulation as described can be more readily understood by considering each sequence as comprising a row of a matrix. Filler characters are provided wherever necessary to make row lengths equal. What is sought is an alignment of the matrix rows that maximizes a pre-specified cost function. In an exemplary embodiment, the cost function is defined as the number of columns in which a common character appears at least k times. Other cost functions may be realized by the method.

The sequence alignment method of the present invention proceeds in two stages: 1. motif discovery and 2. pruning and alignment. In the motif discovery stage, the set of input sequences, N, are searched to identify or discover any motifs which may exist in the N input sequences. During the pruning and sequence alignment stage a determination is made regarding whether all or some subset of the motifs discovered in the first stage can be used to align or render the N sequences. More particularly, it must be determined whether one or more identified motifs precludes bringing out the best commonality among the N sequences. If so, one or more offending motifs are pruned or removed from consideration when performing the alignment. Otherwise, if all the motifs are usable then an alignment is formed that utilizes or respects all the identified motifs.

1. Motif Discovery

The method of motif discovery used in the present invention is described in patent application Ser. No. 60/062,306, herein incorporated by reference in its entirety. During the motif discovery stage, motifs are identified or discovered from the N input sequences. A motif is defined in the present context as a pattern that appears in two or more sequences. In most instances a very large number of motifs will be identified. The present invention can accommodate this result at the expense of processing time. To alleviate this potential bottleneck, however, the method, in an alternate embodiment, may also search for only irredundant motifs. Irredundant motifs are a special sub-class of motifs, whose number is only quadratic in input size. A polynomial time algorithm may then be used to extract the irredundant motifs from the input thereby bounding the extraction time.

2. Pruning and Sequence Alignment

A pruning and sequence alignment stage follows the motif discovery stage. At this stage any "offending" motifs are identified and removed from consideration during sequence alignment. Offending motifs are defined as those motifs which preclude performing a sequence alignment which achieves the best commonality among the N sequences. Offending motifs are identified by the method as a consequence of performing three infeasibility tests. The three tests are; 1. a pairwise compatibility test, 2. a smallest cycles test, and 3. a closed path with inconsistencies test. Each will be described in detail. For each of the three tests, one or more offending motifs may be identified. Each group of identified offending motifs is said to form an infeasible set. Therefore, the infeasible sets, when found, comprise one or more offending motifs which violate the respective infeasibility test.

2.1 Pairwise Compatibility Test (Determination of the 1st Infeasible Set)

The first infeasible set is comprised of those offending motifs which fail the test for pairwise compatibility. Those offending motifs are identified in pairs and are therefore defined as pairwise incompatible or forbidden pairs. The pairwise compatibility test will be performed for only those motifs, identified at stage 1, which occur simultaneously in at least one input sequence. The pairwise compatibility test is comprised of two sub-tests 1) a domain crossing mismatch test, and 2) an overlap mismatch test. Each test will be explained by way of example.

With specific reference to the first test, domain crossing mismatch, assume the following sequences are input to the process;

Sequence 1: "<u>A B C</u> D E"

Sequence 2: "<u>D E</u> A B C"

Two motifs are identified from sequences one and two, they are "A B C", and "D E". By virtue of the relative positions of the two motifs in the respective sequences it is apparent that there is no feasible sequence alignment of sequence one and two that will permit the simultaneous alignment of the two motifs. This incompatibilty arises as a consequence of the juxtaposition of the two motifs in the respective sequences. As a consequence, the motif pair fails the domain crossing mismatch test. Failing the first sub-test of the two-part pairwise incompatibility test is sufficient to declare the motif pair incompatible and removes the necessity of performing the second sub-test.

The second test, overlap mismatch, is also illustrated by example. Given the two sequences, Sequence 1: "A B C E E"
Sequence 2: "A C E E F",
two motifs are identified. They are "A . . E", where the dots indicate don't care characters and "C E E". It is apparent that no alignment of the two sequences will respect the simultaneous alignment of the two motifs because alignment of one motif requires a linear translation of one sequence such that alignment of the other motif is prevented. When that situation occurs an overlap mismatch between the two motifs exists. From the pairwise incompatibility test a first infeasible set is generated, assuming there is at least one pair of motifs which violate the test.

Graph Construction

A directed graph is then constructed. Directed graphs are well known in the art, example of such graphs may be found in chapter 23 of Introduction to Algorithms by T. H. Cormen, C. E. Leiserson, and R. L. Rivest, herein incorporated by reference. The vertices of the directed graph correspond to the motifs discovered at the first stage, motif discovery. That is, each vertex in the graph will correspond to one of the discovered motifs. Further, a directed edge will connect two vertices (motifs) in the graph only when there exists at least one input sequence in which the corresponding motifs occur together. Stated in the alternative, if two motifs do not appear together in any of the N input sequences, no directed edge will connect their associated vertices in the graph. Directed edges are defined in the graph by an arrow which points to one of the two vertices it connects. For example, for motifs A and B, their connectivity in the graph may be represented as;

Vertex A (Motif A)→Vertex B (Motif B)

The directionality of the directed edge indicates that motif A is to the left of motif B in the input sequence list. For those motif pairs which fail the pairwise compatibility test, however, no left/right designation is possible, for reasons stated above, and as a consequence the directed edge will be labeled as a "forbidden pair" with no arrow designation. For all other motif pairs in the graph having an associated directed edge, that directed edge will be labeled as either overlap or non-overlap. An edge will be labeled overlap whenever any instance of the two motifs overlap in any one of the N input sequences. For example, motifs "A B . D" and "C D E" overlap in the sequence 1 below but not in sequence 2.

Sequence 1="A B C D E"
Sequence 2="A B X D Y G H C D E"

Note that irrespective of whether the directed edge is labeled overlap or non-overlap, the motifs associated with that edge are pairwise compatible. Only those edges labeled "forbidden pair" have associated motifs which are pairwise incompatible.

Referring now to FIGS. 1a and 1b, a directed graph 7 is illustrated in FIG. 1a. The graph 7 is constructed from an input sequence list 8, illustrated in FIG. 1b, having three input sequences 8, N=3, and five identified motifs 9.

Each identified motif 9 corresponds to a respective vertex in the directed graph 7 as illustrated in FIG. 1a. Directed edges DE 20–38 are illustrated and serve to connect the identified motifs 9. The arrow 13 associated with each directed edge indicates that the motif associated with the vertex being pointed to by the arrow 13 occurs to the right of the motif whose vertex is located on the opposite side of the directed edge. For example, directed edge 20 with associated arrow 13 indicates that the directionality of the edge is from vertex 10 to 12. The directionality specifies that motif (vertex) 10 is located to the left of motif (vertex) 12 in the sequence list 8. In addition to the directionality associated with each edge, additional labeling is illustrated. Most edges in the graph have a dual identification with the first identifier characterizing the respective motifs as "forbidden pair", "overlap", or "non-overlap", and a second identifier describing a distance metric, shown in brackets 15 in the directed graph 7. The distance metric is a positive integer which is a measure of the minimum separation distance in the input sequence list 8 between the two motifs (vertices) connected by the directed edge. The separation distance is measured from the first character in each measured motif string. The computation of the distance metric for a directed edge is best illustrated by example.

Assume, for example, a directed edge connects two vertices (motifs); "A B C" and "D E". Further assume that the two motifs were identified from the following input sequences;

```
           - - - ->    +5     <- - - -
Sequence 1 = "ABC X X DE"
Sequence 2 = "ABC X X X DE"
           - - - ->    +6     <- - - -
```

As illustrated, the distance, measured from the first character in each string, between the first motif, "A B C", and the second motif, "D E", is +5 in the first sequence and +6 in the second sequence. The distance metric that would be assigned to the directed edge in the graph would be the minimum of the two distances , (i.e. +5=min(+5,+6)), in the example shown.

Directed edge 20 in the graph 7 is exemplary of the dual labeling associated with a directed edge not labeled as a "forbidden pair". Directed edge 20 is labeled "overlap (2)" indicating that the two motifs overlap each other in the sequence list 8 with a distance metric measure of +2. A distance metric will be computed for each directed edge in the graph not labeled "forbidden pair". A distance metric is neither required, nor logically assignable to edges labeled "forbidden pair". Directed edges DE 22, DE 24, and DE 28–38 are each assigned a non-overlap label, with only edge 36 being explicitly illustrated for purposes of clarity of presentation.

The following pseudo-code generally describes the construction and labeling of directed edges between vertices (motifs) in the directed graph.
For every motif $p_i$, do
For every motif $p_j$, not equal to $p_i$, do
  Does there exist a sequence in which both $p_i$ and $p_j$ occur
  No: No directed edge exists between $p_i$ and $p_j$
  Yes: Are motifs $p_i$ and $p_j$ pairwise compatible?
    No: Assign label forbidden to edge $v_i$ $v_j$
  Yes: Do motifs $p_i$ and $p_j$ overlap?
    Yes: Assign label overlap to edge $v_i$ $v_j$
    No: Assign label non-overlap to edge $v_i$ $v_j$ Once a directed graph is constructed the method performs the second and third tests for infeasiblity. The second and third tests for infeasibility are distinguishable from the first test in that the first test is directed to identifying offending pairs of motifs. The second and third tests are both directed to identifying groups of three or more offending motifs.

2.2 Smallest Cycles Test (Determination of the 2nd Infeasible Set)

The second test for infeasibility will now be explained. The second test is directed to finding smallest cycles in the graph. A smallest cycle constitutes a closed loop in the graph wherein a closed loop is defined as any path that originates at some starting vertex and follows a path through at least two additional distinct vertices and returns to the starting vertex. Closed loops are distinguishable from closed paths which will be defined with reference to the third test for infeasibility, closed path inconsistencies.

Figure 2:
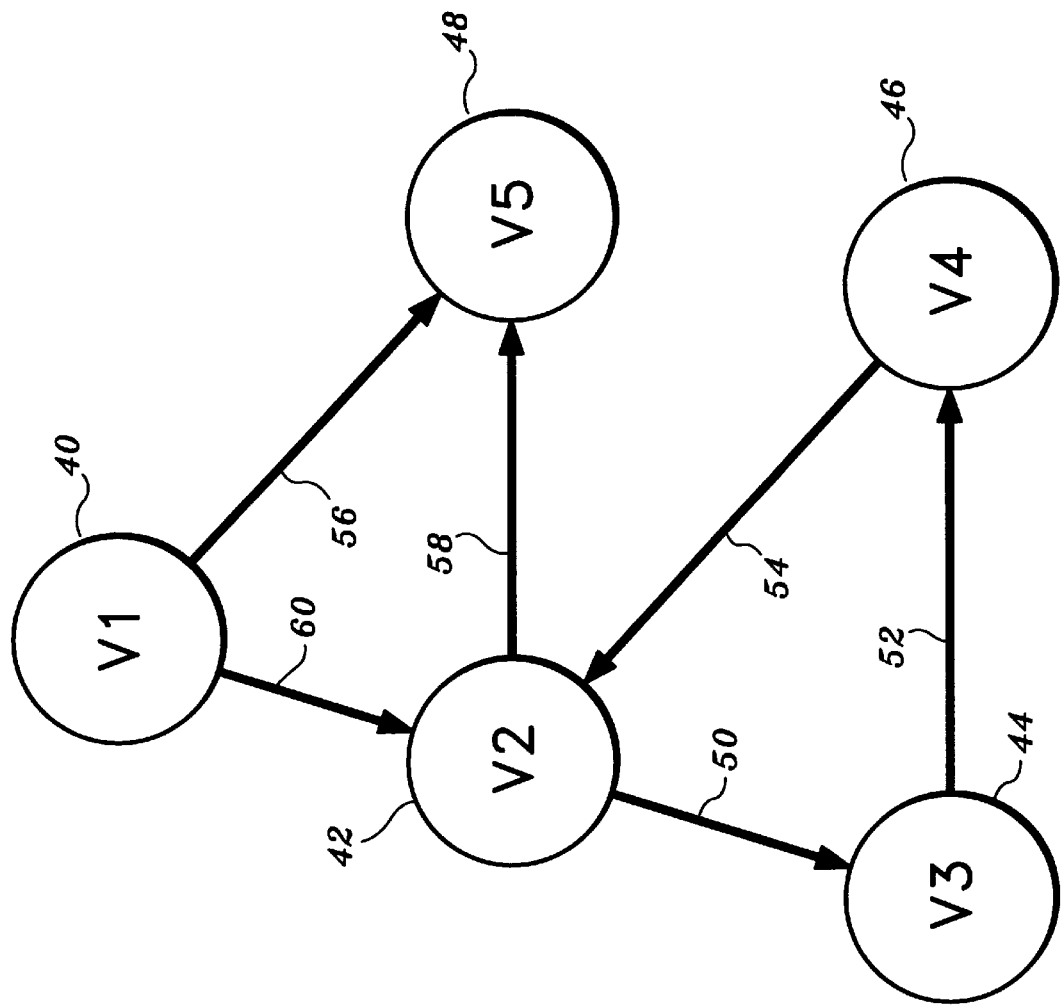
FIG. 2 is a directed graph that illustrates an infeasible set of the second type, closed cycle.

Referring now to FIG. 2, an example of a cycle (closed loop) is illustrated. In FIG. 2, a directed graph is shown comprising five vertices, V1 40, V2 42, V3 44, V4 46, and V5 48 and six directed edges DE 50, DE 52, DE 54, DE 56, DE 58, and DE 60. Each vertex corresponds to a motif identified at stage one, motif discovery. A cycle is illustrated in FIG. 2 by following the path defined by directed edges DE 50, DE 52, and DE 54. The directed edges lead from a starting vertex, V2 42 to one or more intermediate vertices, defined by V3 44 and V4 46 in FIG. 2, and back to the start vertex V2 42. By contrast, the path defined by directed edges DE 60, DE 58, and DE 56 do not define a cycle or closed loop because starting at any node, the directed edges do not eventually lead back to a start node. If, however, in the directionality of the directed edge DE 56 were reversed then a closed cycle would exist for edges DE 60, DE 58 and DE 56.

The method identifies any potential closed loops or cycles in the graph by performing a depth first search. Depth first searches are well known in the art and the method steps for performing the search is well documented in the literature, an example of which can be found in chapter 23 of *Introduction to Algorithms*, herein incorporated by reference in its entirety.

As the depth first search is being performed, any offending motifs which violate the second test for infeasibility (closed loops) are identified and grouped into an infeasible set of the second type (closed loops).

2.3 Closed Path with Inconsistencies Test (Determination of the 3rd Infeasible Set)

The third test for infeasibility will now be explained. The third test is directed to finding all closed paths with inconsistencies in the graph. A closed path may be generally defined as two or more distinct paths having a common origin and destination vertex. An inconsistent closed path may then be defined as an identified closed path which violates the closed path infeasibility test. The details associated with the infeasibility test for closed paths will be described in detail later.

Figure 3:
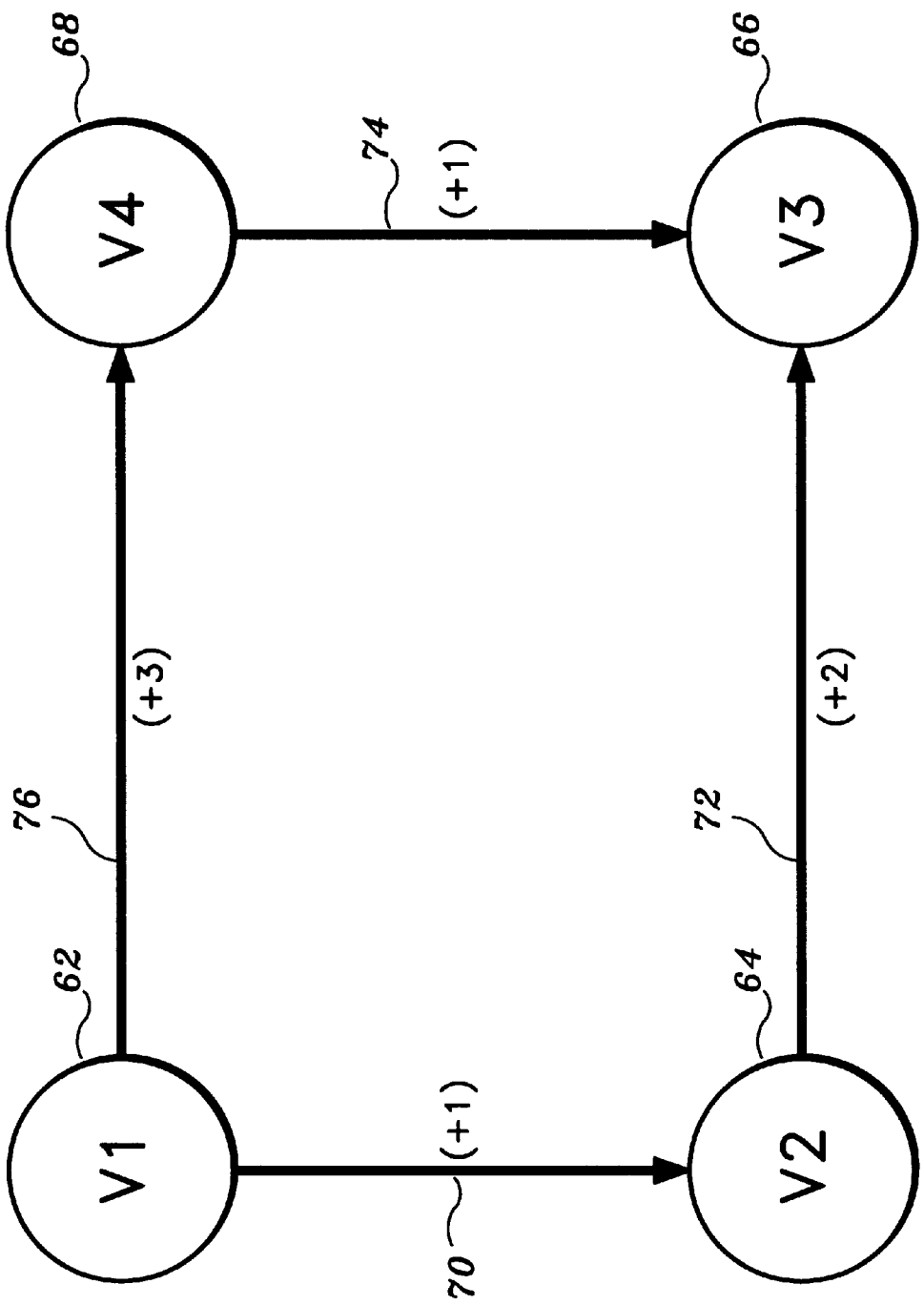
FIG. 3 is a directed graph that illustrates an infeasible set of the third type, closed path inconsistency.

Referring to FIG. 3, a directed graph illustrating an inconsistent closed path is shown. The graph is comprised of four vertices; V1 62, V2 64, V3 66, and V4 68 and four directed edges DE 70, DE 72, DE 74, and DE 76. The graph illustrates two paths P1 and P2 starting from vertex V1 62 and terminating at vertex V3 66. Path P1 is defined by directed edges DE 70 and DE 72, and path P2 is defined by edges DE 76 and DE 74.

The present invention identifies all closed paths in the graph by performing a breadth first search. A breadth first search is performed for each vertex in the graph. That is, for the four vertices illustrated in FIG. 3, four separate breadth first searches will be performed utilizing one of the four vertices as the start vertex in each iteration. Breadth first searches are well known in the art and the method steps for performing the search is well documented in the literature, an example of which can be found in chapter 23 of *Introduction to Algorithms*, herein incorporated by reference in its entirety. The objective of the algorithm, simply stated, is given a graph and a distinguished source vertex, a breadth first search systematically explores the edges of the graph to discover every vertex that is reachable from the source vertex.

As the breadth first search is being performed to identify closed paths, the third test for infeasibility (closed path inconsistencies) is performed in parallel. That is, as the breadth first search is being executed, necessary vertex information is provided as input to the third test for infeasibility which is performed in parallel with the breadth first search. In particular, the third test receives information from the breadth first search concerning the identification of any closed paths. A closed path is identified whenever there exists two or more paths, p={1, . . . M}, from any source vertex V1 in the graph to any destination vertex V2. (i.e. p=2 in FIG. 3). A path distance metric, $pdm_i$, is computed for each path i as the sum of the distance metrics of each directed edge in the path, $pdm_i=dme_1+dme_2+dm_i$ . . .

Referring again to FIG. 3, a path distance metric would be computed for paths 1 and 2. The path distance metric for path 1, $=pdm_i+3$, is computed as the sum of the distance metric for directed edge DE 70, ($dme_{70}=+1$) and the distance metric for directed edge DE 72 ($dme_{72}=+2$). The path distance metric for path 2, $pdm_2=+4$. The path distance metric information, along with other data, is used by the infeasibility test for determining whether a closed path is inconsistent. In particular, for a closed path comprising a set S of paths p={1, . . . M}, each path p from the set S will be individually compared with every other path in the set S to determine whether the closed path is inconsistent. For example, assume that three paths, p={1,2,3}, are identified while performing the breadth first search, with a common start and destination vertex. The third test for infeasibility would first compare paths 1 and 2. When path 3 is identified by the search algorithm, the infeasibility test would then compare paths 1 and 3 and 2 and 3. If during any particular path comparison it is determined that the test is violated, no further comparisons are required and the motifs comprising the closed path are determined to be offending motifs of the third type (closed paths with inconsistencies).

Figure 4:
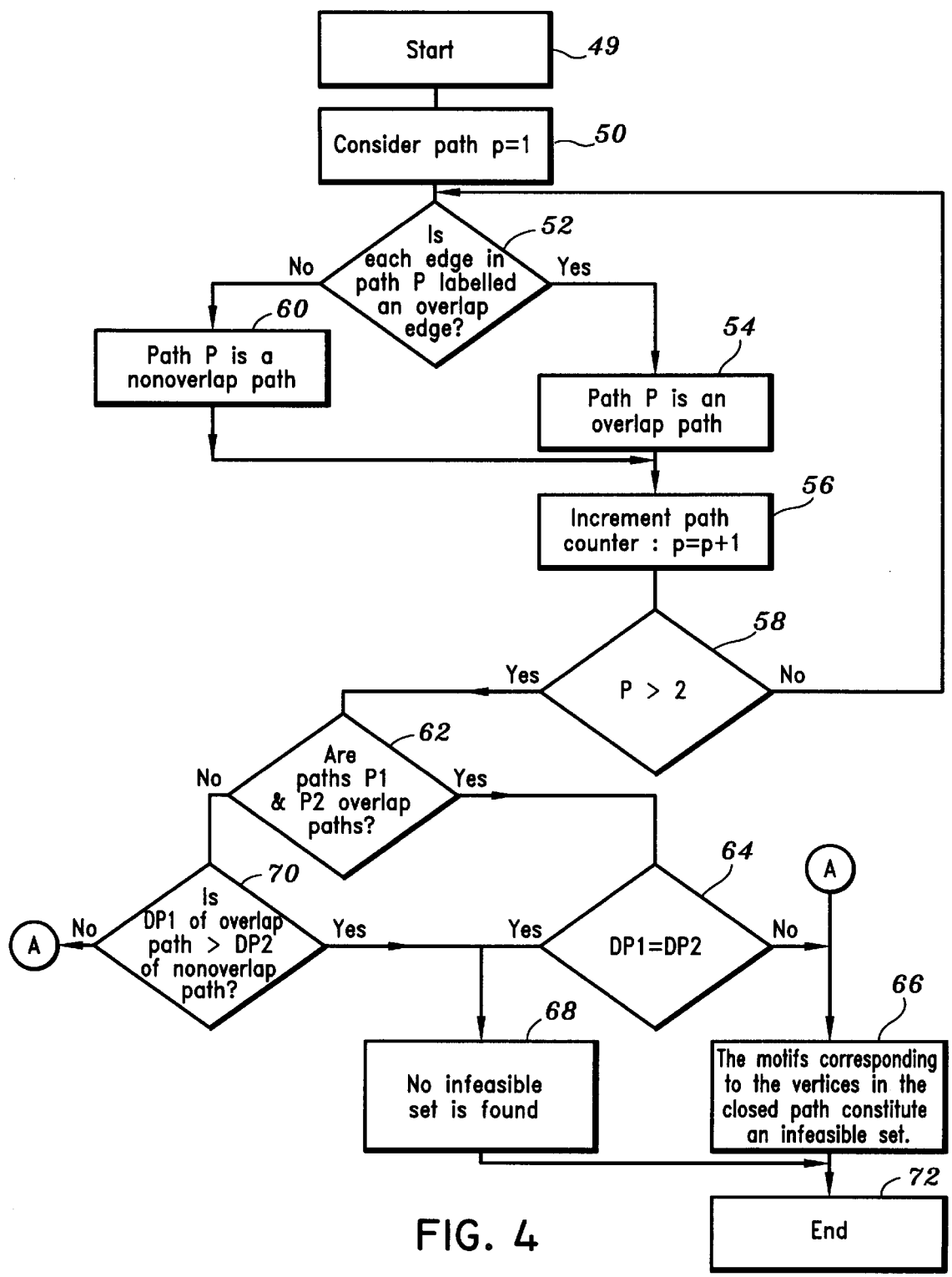
FIG. 4 is a flow diagram for a two-path comparison to identify a closed path inconsistency.

Referring now to FIG. 4, the method steps illustrating the details of performing the third test of infeasiblity for two paths identified by the breadth first search algorithm is shown. At step 80, two paths are identified by the breadth first search algorithm, P1 and P2. At step 82, a determination is made as to whether the first path, P1, is an overlap or a non-overlap path. At step 84, a similar determination is made as to whether the second path, P2, is an overlap path or a non-overlap path. At decision step 86, a determination is made as to whether both paths, P1 and P2, are overlap paths. If both paths P1 and P2 are overlap paths a branch occurs to decision step 92 where a determination is made as to whether the path distance metrics for paths 1, dp1, and 2, dp2, are equal. If not, a branch occurs to step 94 where it is determined that the motifs comprising the closed path constitute an infeasible set. The process then terminates at step 96. If, however, dp1=dp2, the distance metrics for paths 1 and 2 are found to be equal, then a branch occurs to step 93. At step 93 it is determined that the motifs corresponding to the vertices in the closed path do not constitute an infeasible set. The process then terminates at step 96.

At decision step 86, if either path P1 or P2 is determined not to be an overlap path then a branch is taken to decision step 88. At decision step 88 a determination is made as to whether the distance metric for the path determined to be the overlap path is greater than the distance metric for the path determined to be the non-overlap path. If true, a branch occurs to step 93. Otherwise a branch occurs to step 94. The process terminates at step 96.

2.a Pruning Stage

Upon completing the test for the third type of infeasible set, closed path with inconsistencies, the three infeasible sets of offending motifs are completely determined. Having identified all of the offending motifs, the method of the present invention then prunes or removes at least one offending motif from each identified infeasible set to both allow the sequences to be aligned and to maximize a pre-specified cost function. In the exemplary embodiment, the cost function is defined as the sum of all the matching characters in the columns of the alignment in which at least K characters are identical. Other user defined cost functions include, but are not exclusive to; 1. the sum of the columns of the alignment in which at least K characters are identical, and, 2. retaining a maximum number of motifs for consideration at the alignment stage (i.e. pruning a minimum number of motifs). Other realizable cost functions may be considered by the method.

To maximize the cost function, as defined by the exemplary embodiment, defined as;

Cost Function: the sum of all the matching characters in the columns of the alignment in which at least K characters are identical to the method of the present invention utilizes a mathematical algorithm, defined in the prior art as the weighted set-covering algorithm, discussed at length in chapter 37 of Introduction to Algorithms, and herein incorporated by reference in its entirety.

Application of the weighted set-covering problem to the problem of removing offending motifs will now be explained by way of example. As was described, a number of offending motifs were identified and collected into one or more of the three infeasible sets.

1. Pairwise incompatible,
2. Closed cycles, and
3. Closed path with inconsistencies.

Assume the first test of infeasibility, forbidden pairs (pairwise compatibility), identified a single pair of offending motifs thereby generating a first infeasible set;

1st infeasible set: X={M3, M4}

Assume the second test of infeasibility, smallest cycles, identified three offending motifs thereby generating a second infeasible set;

2nd infeasible set: Y={M1, M2, M7}

Assume the third test of infeasibility, closed paths with inconsistencies, identified three offending motifs thereby generating a third infeasible set;

3rd infeasible set: Z={M3, M5, M7}

It is notable that the offending motifs which are the respective members of sets X, Y, and Z are not disjoint. That is, motifs M3 and M7 in the example provided, appear in two of the three categories. In general, a motif may appear in one, two, or all three of the sets.

Application of the weighted set covering problem to the method of the present invention in the context of the present example is as follows. From the three identified infeasible sets X, Y, and Z, derived as a result of performing the infeasibility tests, a union set A is formed where A={X, Y, Z}. In addition to defining union set A, sets $B_{m1}$ through $B_{m7}$ are defined, indicating which infeasible set(s) each offending motif, M1–M7, belongs to. For example, set $B_{m1}$ describes that motif M1 is a member of only infeasible set Y, smallest cycles.

$B_{m1}$={Y}
$B_{m2}$={Y}
$B_{m3}$={X, Z}
$B_{m4}$={Z}
$B_{m5}$={X}
$B_{m7}$={Y, X}

As a further example, $B_{m3}$={X, Z} indicates that offending motif M5 is a member of both the first and third infeasible sets, forbidden pairs and closed paths with inconsistencies.

In terms of an unweighted set-covering problem solution, the objective of the present method is to find a minimum number of B sets that covers A. That is, what combination B sets will completely characterize set A where A is the set defined as the union of X, Y, and Z. For the present example, one possible solution is the combination of B sets {$B_{m2}$ and $B_{m3}$} where $B_{m2}$ defines Y and $B_{m3}$ defines X and Z. Other possible solutions include {$B_{m7}$ and $B_{m}$}, or {$B_{m1}$ and $B_{m3}$}. These and other solutions are realizable from the example above.

Any of the above solutions would satisfy the unweighted set-covering problem. To satisfy the weighted set-covering problem, however, removing B sets requires additional considerations. In particular, the weighted set-covering problem associates a weight with each identified B set. Furthermore, the weight is computed differently, depending upon the particular pre-specified cost function that is to be maximized. For the cost function defined by the exemplary embodiment the weight is computed as a multiplication of the number of solid characters of the motif represented by that B set multiplied by the number of sequences in which it appears. For example if motif M2 of set $B_{m2}$ was "A B . D", the number of solid characters in the motif is three. If motif M2 appeared in two of the N input sequences then the weight associated with $B_{m2}$ would be 3*2=6. A weight value is similarly calculated for all identified B sets.

Having determined weights for each of the B sets, maximizing the pre-specified cost function of the exemplary embodiment then involves removing, or pruning, those B sets from consideration in the alignment stage which minimize the collective weight. For example, three possible solutions were explicitly defined for the present example, additional solutions are identifiable but not cited for the sake of clarity:

1. {$B_{m2}$ and $B_{m3)}$ with associated weight w1
2. ($B_{m1}$ and $B_{m3)}$ with associated weight w2
3. {$B_{m4}$ and $B_{m1)}$ with associated weight w3

The selected solution, however, would be selected as the one whose associated weight is minimum, min(w1,w2,w3).

3.b Alignment Stage

At the alignment stage, once the offending motifs (B sets) are removed from consideration in accordance with the weighted set-covering method, the N input sequences may then be aligned without conflict. For those offending motifs which are removed from further consideration their associated vertices in the graph will be pruned leaving only feasible vertices (motifs). The resulting directed graph is then used to determine step 1 defined below.

To render an alignment of the N sequences, each sequence is individually analyzed to determine two things; 1. the relative positions of any feasible motif contained in that sequence, and 2. the filler positions, where a filler position is a position in the sequence not occupied by a feasible motif. Knowing the motif and filler positions, each sequence is then aligned with every other sequence such that the feasible motifs are properly aligned. Fillers or gaps may be necessary to achieve the final alignment.

The alignment procedure described is further explained by way of example. Assume two sequences, N=2, are input to the method, described as;

Sequence 1: a b c d e f g h i j k l
Sequence 2: c d e x y z p q r g h i t u

Further assume that after the pruning stage, the feasible motifs (vertices) comprise "c d e" and "g h i". The relative position of Motif "c d e" in sequences 1 and 2 is determined to occupy positions 3–5 in sequence 1 and positions 1–3 in sequence 2. Similarly the relative position of motif "g h i" occupies position 7–9 in sequence 1 and 10–12 in sequence 2. The relative position of the fillers may then be determined. Fillers occupy positions 1–2, 6, 10–12 in sequence 1 and 4–9, and 13–14 in sequence 2. With that information fillers or gaps are appropriately inserted to align the two sequences as shown;

Sequence 1: a b c d e f . . . g h i j k l
Sequence 2: c d e x y z p q r g h i t u Note that the two sequences align without conflict as a consequence of each of the respective motifs being feasible.

Referring now to FIG. 5, a sample of some experimental results for the method of the present invention are illustrated. The experimental results pertain to the alignment of a large number of sequences with biological relevance. The input sequences are not shown. In FIG. 5, uppercase letters depict aligned characters and lowercase letters are portions of the input sequence that the method has not taken into account. The dots ('.') represent don't cares and the dashes represent the gaps enforced by the algorithm. Furthermore, some portions of the input have been removed to avoid clutter in the figure.

Results are illustrated on three sets of data: the first set is on a highly similar data set (histones) and the second set is on a fairly dissimilar (cytosine-specific DNA methylases list in PROSITE database (Release 13 entry accession #PS00094) data set, and a set of plant hemoglobins (listed in the PROSITE database Release 13 entry accession #PS00208). The first data set has 20 protein sequences of about 200 residues each with an alignment number K=10. The size of the resulting fensible set of motifs was found to be 22 for a maximal motif size of N=648. The second has 46 protein sequences with lengths going up to 500 residues, with an alignment number of K=18. The size of the resulting set of motifs was found to be 132 for a maximal motif size of N=810. A third set has 21 sequences with about 150 residues each, with an alignment number of K=14. A resulting compatible set of 42 motifs were identified from N=873 non-redundant motifs.

With particular reference to the first set of data, the method successfully identifies COREHISTONE-3 FOLDS. These folds represent sub-structures contained within the proteins. With reference to the second set of data, the alignment identifies the blocks that correspond well to the consensus blocks for the protein as identified in BLOCKS entry number BL0094 of BLOCKS database. With reference to the third set of data, the method identifies the known secondary structures (HELICES) present in the globin family members.

In the examples, some of the sequences have been truncated in the alignment and the output runs across multiple pages due to the size.

As will be obvious to those skilled in the art, the present invention can be practiced with a wide variety of modifications and variations, and is not limited except as specified in the accompanying claims.

What is claimed is:

1. A method for aligning characters in character sequences, said method steps comprising:
   identifying a plurality of motifs from the character sequences based on sub-sequences in the character sequence;
   removing a subset of motifs from said plurality of identified motifs which prevent alignment of the character sequences; and
   aligning the character sequences based on the remaining motifs.

2. The method according to claim 1, further comprising receiving as input from a user an alignment number, K, constraining the sequence alignment to have at least K of N character sequences agree on a character in said character sequence alignment.

3. The method according to claim 1, wherein the step of identifying said plurality of motifs from the character sequences comprises identifying repeated character patterns that appear in at least two of said character sequences.

4. The method according to claim 1, wherein said plurality of motifs identified from said character sequences are irredundant motifs.

5. The method according to claim 1, wherein the step of removing a subset of motifs comprise those motifs whose removal maximizes the number of sequence characters in columns in the sequence alignment in which at least K seuquence characters are identical.

6. The method according to claim 5, wherein a weighted set covering algorithm is performed to maximize the number of sequence characters in each column in the sequence alignment in which at least K sequence characters are identical.

7. The method according to claim 1, wherein the step of removing a subset of motifs comprise those motifs whose removal maximizes the number of characters in each column in the sequence alignment in which at least K characters are identical.

8. The method according to claim 6, wherein a weighted set covering algorithm is performed to maximize the number of columns in the sequence alignment in which at least K characters are identical.

9. The method according to claim 1, wherein the step of removing a subset of motifs from said plurality of identified motifs further comprises identifying offending motifs by constructing a directed graph comprising a plurality of vertices and directed edges between said plurality of vertices, wherein each of said plurality of vertices corresponds to one of said plurality of motifs.

10. The method according to claim 9, wherein a first vertex in said directed graph will be connected to a second vertex when the motifs corresponding to the respective first and second vertexes occur simultaneously in at least one of said plurality of input sequences.

11. The method according to claim 9, wherein the step of removing a subset of motifs further comprises identifying offending motifs which violate one or more infeasibility tests from said directed graph.

12. The method according to claim 11, wherein said one or more infeasibility tests include a pairwise incompatibility test, a smallest cycles test, and a closed paths with inconsistencies test.

13. The method according to claim 12, wherein said smallest cycles test comprises a depth first search on said directed graph.

14. The method according to claim 12, wherein said closed paths with inconsistencies test comprises a breadth first search on said directed graph.

15. The method according to claim 12, wherein said pairwise incompatibility test further comprises a domain crossing mismatch test and an overlap mismatch test.

16. The method according to claim 15, wherein said domain crossing mismatch test further comprises identifying a pair of motifs comprising a first motif and a second motif, where the position of said first motif is to the left of said second motif in a first character sequence from said character sequences, and where the position of said first motif is to the right of said second motif in a second character sequence from said character sequences.

17. The method according to claim 16, wherein said overlap mismatch test further comprises identifying a first motif and a second motif in a first sequence and a second sequence; and determining whether all possible alignments of said first motif in said first and second sequences precludes the simultaneous alignment of said second motif in said first and second sequences.

18. The method according to claim 1, wherein the step of aligning the character sequences is performed simultaneously.

19. A method for aligning characters in character sequences, said method steps comprising:

identifying a plurality of motifs from said character sequences;

identifying offending motifs from said plurality of motifs, wherein said offending motifs prevent sequence alignment of the character sequences;

removing at least one offending motif from consideration at a sequence alignment stage to maximize a pre-specified cost function, wherein the remaining motifs define a feasible set of motifs; and aligning said character sequences from said feasible set of motifs.

20. The method according to claim 19, further comprising receiving as input from a user an alignment number, K, constraining the sequence alignment to have at least K of N character sequences agree on a character in said character sequence alignment.

21. The method according to claim 19, wherein the step of identifying motifs from the character sequences comprises identifying repeated character patterns that appear in at least two character sequences.

22. The method according to claim 19, wherein the pre-specified cost function maximizes the number of sequence characters in columns in the sequence alignment in which at least K sequence characters are identical, wherein K defines an alignment number with some predefined value greater than or equal to 2.

23. The method according to claim 19, wherein the step of identifying offending motifs from said plurality of motifs further comprises constructing a directed graph comprising a plurality of vertices and directed edges between said plurality of vertices, each of said vertices corresponding to one of said plurality of identified motifs.

24. The method according to claim 19, wherein the step of removing a subset of motifs further comprises identifying offending motifs which violate one or more infeasibility tests from said directed graph.

25. The method according to claim 24, where said one or more infeasibility tests comprise a forbidden pairs test, a smallest cycles test, and a closed paths with inconsistencies test.

26. The method according to claim 25, wherein said forbidden pairs test further comprises a domain crossing mismatch test and an overlap mismatch test.

27. The method according to claim 25, wherein said smallest cycles test comprises a depth first search on said directed graph.

28. The method according to claim 25, wherein said closed paths with inconsistencies test comprises a breadth first search on said directed graph.

29. The method according to claim 26, wherein said domain crossing mismatch test further comprises identifying a pair of motifs comprising a first motif and a second motif, where the position of said first motif is to the left of said second motif in a first character sequence from said character sequences, and where the position of said first motif is to the right of said second motif in a second character sequence from said character sequences.

30. The method according to claim 26, wherein said overlap mismatch test further comprises identifying a first motif and a second motif in a first sequence and a second sequence; and determining whether all possible alignments of said first motif in said first and second sequences precludes the simultaneous alignment of said second motif in said first and second sequences.

31. A computer program device readable by a machine, tangibly embodying a program of instructions executable by the machine to perform method steps for aligning characters in character sequences, said method steps comprising:

identifying a plurality of motifs;

identifying offending motifs from said plurality of motifs, wherein said offending motifs prevent sequence alignment of the character sequences;

removing at least one offending motif from consideration at a sequence alignment stage, wherein those motifs not removed from said plurality of motifs define a feasible set of motifs; and aligning said character sequences from said feasible set of motifs to maximize a pre-specified cost function.

32. The method according to claim 31, further comprising receiving as input from a user an alignment number, K, constraining the sequence alignment to have at least K of N character sequences agree on a character in said character sequence alignment.

33. The method according to claim 31, wherein the step of removing said at least one attending motif from said plurality of identified motifs further comprises identifying offending motifs by constructing a directed graph comprising a plurality of vertices and directed edges between said plurality of vertices, wherein each of said plurality of vertices corresponds to one of said plurality of motifs.

34. The method according to claim 33, wherein a first vertex in said directed graph will be connected to a second vertex when the motifs corresponding to the respective first and second vertexes occur simultaneously in at least one of said plurality of input sequences.

35. The method according to claim 33, wherein the step of removing said at least one offending motif further comprises identifying offending motifs which violate one or more infeasibility tests from said directed graph.

36. The method according to claim 35, wherein said one or more infeasibility tests include a pairwise incompatibility test, a smallest cycles test, and a closed paths with inconsistencies test.

37. The method according to claim 35, wherein said smallest cycles test comprises a depth first search on said directed graph.

38. The method according to claim 35, wherein said closed paths with inconsistencies test comprises a breadth first search on said directed graph.

39. The method according to claim 35, wherein said pairwise incompatibility test further comprises a domain crossing mismatch test and an overlap mismatch test.

* * * * *